United States Patent [19]
Bright et al.

[11] Patent Number: 6,016,689
[45] Date of Patent: *Jan. 25, 2000

[54] AEROSOL-GENERATED SOL-GEL DERIVED THIN FILMS AND APPLICATIONS THEREOF

[75] Inventors: Frank V. Bright; Luis A. Colon, both of Amherst; Jeffrey D. Jordan, Buffalo, all of N.Y.; Richard A. Dunbar, Canoga Park, Calif.

[73] Assignee: The Research Foundation of Suny at Buffalo, Amherst, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/752,460

[22] Filed: Nov. 18, 1996

[51] Int. Cl.⁷ ....................................................... G01N 7/00
[52] U.S. Cl. ............................................................ 73/31.05
[58] Field of Search .................................. 73/23.31, 31.01, 73/31.05; 422/83, 86, 94, 98, 55, 57, 60; 435/180, 182, 176; 436/518, 524, 527, 535

[56] References Cited

U.S. PATENT DOCUMENTS

| | | |
|---|---|---|
| 4,822,465 | 4/1989 | Jones et al. . |
| 5,151,110 | 9/1992 | Bein et al. . |
| 5,300,564 | 4/1994 | Avnir et al. . |
| 5,326,449 | 7/1994 | Cunningham . |
| 5,577,137 | 11/1996 | Groger et al. . |
| 5,670,949 | 9/1997 | Kirby et al. . |

FOREIGN PATENT DOCUMENTS 405045321  2/1993  Japan ..................................... 73/31.05

OTHER PUBLICATIONS

Collino et al., Journal of Sol–Gel Science and Technology 7(1–2):81–85(1996).

Jordan et al., Analytica Chimica Acta 332:83–91 (1996).

*Primary Examiner*—Robert Raevis
*Attorney, Agent, or Firm*—Braman & Rogalskyj, LLP

[57] ABSTRACT

A sensor having a substrate overlayed with a sol-gel layer, a chemical sensing species deposited upon the sol-gel layer, and a thin film of a second sol-gel layer overlaying and entrapping the species. The effect of this sensor is that the species exhibits a significant portion of its intrinsic function over a period of time. In yet another embodiment of the subject invention, a method is disclosed to form a thin sol-gel layer upon an ambient substrat. This method ensures the integrity, stability and functionality of the chemical sensing species within the sol-gel layers.

18 Claims, 12 Drawing Sheets

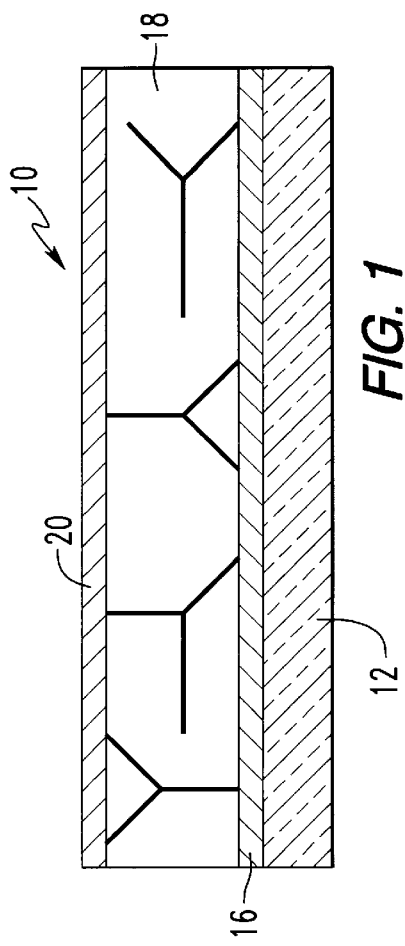
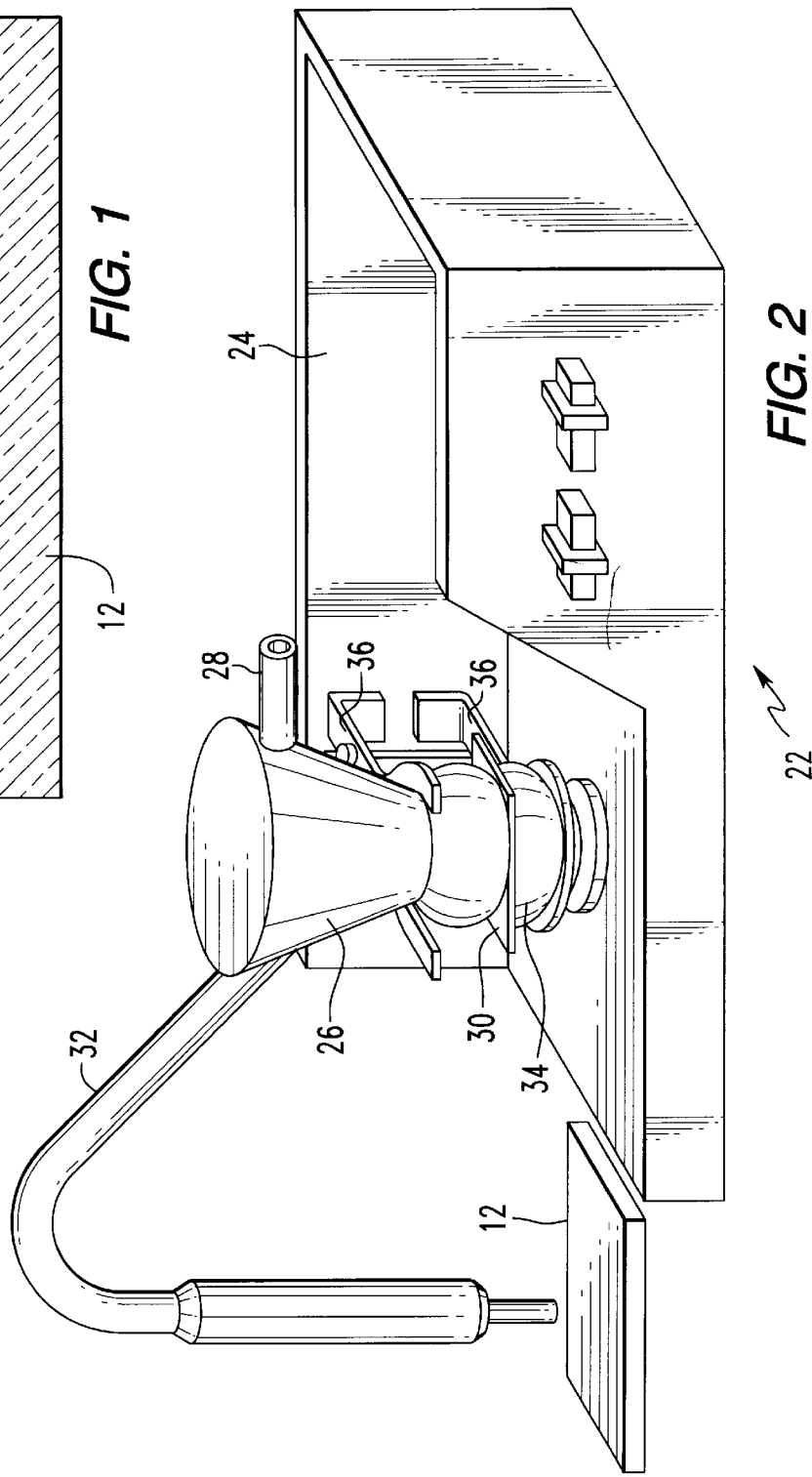

AEROSOL-GENERATED SOL-GEL DERIVED THIN FILMS AND APPLICATIONS THEREOF

This invention was made with support from the National Science Foundation and its contract numbers are:DMR-9303032, CHE 9300694, and CHE-9626636; and the Office of Naval Research and its contract number is N00014-96-1-0501. The Federal Government may retain certain rights in this invention.

TECHNICAL FIELD

The application of sol-gel layers upon a substrate and applications thereof

BACKGROUND OF THE INVENTION

A chemical, immunological or biological sensor instrument is selective for a particular target analyte. Such a sensor can, and often does, contain an immobilized chemical sensing species. The chemical sensing species is an organic, inorganic or biological recognition element that selectively recognizes a target analyte. In order for the sensor to operate, the analyte and the immobilized species must be able to bind together to produce an optical, mass, or electrochemical response related to the concentration of the desired analytes. The selection of particular chemical sensing species for a targeted analyte is well known.

What is not well known, is a method to effectively immobilize the chemical sensing species while maintaining its affinity and intrinsic function over time. There are various techniques to immobilize the species. These techniques can be classified generally as covalent and non-covalent attachment techniques. The covalent technique is initially attractive, but is often tedious, labor intensive, and requires relatively expensive reagents or environmentally unattractive solvents. Further, covalent attachment is dependent on specific functionalities being present on the species such that it can be attached to surface moieties. In other aspects of covalent bonded sensors the recognition chemistry is generally limited to monolayer coverages.

The non-covalent techniques, in contrast, capitalize on entrapping or adsorbing the species to form the sensor. One such technique is a sol-gel process. Sol-gel derived composites serve to entrap the chemical sensing species within a macroscopic solid. Unfortunately, sol-gel based sensors that use monoliths are not practical for most real-world measurements because of the inherently long response times associated with the long, circuitous diffusion pathlength of the analyte and the limited accessibility of an entrapped chemical sensing species to the analyte. In order to exploit the advantages of sol-gels and improve the response times and overall sensor performance, diffusion pathlengths must be decreased and/or the accessibility of the sol-gel entrapped chemical sensing species increased.

Thin sol-gel films, in principle, can solve these pathlength and accessibility matters. Common methods to prepare sol-gel derived thin films include dip and spin casting. These methods entail loading the chemical sensing species directly into the sol solution. Conceptually this is not a problem. Realistically, if the chemical sensing species is expensive or difficult to obtain, this method is wasteful and less attractive. L. L. Hench and J. K. West, Chem Rev., 90 (1990) 33. This method also creates a rough and cracked sol-gel film.

Another method to prepare thin layer films is disclosed in U.S. Pat. No. 3,840,391, by Spitz et al. This method entails preparing a metal-ligand composition in an aerosol generating instrument. The instrument comprises an ultrasonic wave emitter which is placed on the underside of an annular tank containing an ultrasonic-wave transmitting liquid. The instrument also comprises a diaphragm that closes-off an atomization chamber that is constituted by a cylindrical tube provided at the top with a conical end portion in which is inserted a head. The head carries a duct through which the aerosols are discharged. The aerosoled film is then applied upon a heated substrate having a temperature of at least 450° C. In most instances, the heated substrate is a glass plate.

A problem to solve is to provide a sol-gel based sensor that effectively immobilizes a chemical sensing species while maintaining the species' affinity and intrinsic function over time.

Another problem to solve is to provide a method to effectively immobilize the chemical sensing species while maintaining its affinity and intrinsic function over time within a sol-gel film.

Another problem to solve is to provide a new aerosol generation instrument for the deposition of sol-gel derived thin films.

Another problem to solve is to create a relatively smooth and crack-free sol-gel film.

In yet another problem to solve is to control the porosity of the thin sol-gel layer.

Another problem to solve is to control the hydrophobicity or hydrophilicity characteristics of the sol-gel layer.

Another problem to solve is applying a thin sol-gel layer upon a substrate at ambient temperatures to ensure the integrity, stability and functionality of the entrapped chemical sensing species.

SUMMARY OF THE INVENTION

A sensor having a substrate overlayed with a sol-gel layer, a chemical sensing species deposited upon the sol-gel layer, and a thin film of a second sol-gel layer overlaying and entrapping the species. The effect of this sensor is that the entrapped species exhibits a significant portion of its intrinsic function over a period of time. In yet another embodiment of the subject invention, a method is disclosed to produce a uniform thin sol-gel layer upon an ambient substrat. This method ensures the integrity, stability and functionality of the chemical sensing species within the sol-gel layers.

These and other objects, features, and advantages of the invention will become readily apparent from the following description, drawings and appended claims.

BRIEF DESCRIPTION OF THE DRAWINGS

FIG. 1 is a cross-sectional view of a sensor;

FIG. 2 is a schematic of an aerosol deposition instrument;

FIG. 4A is a sensor comprising antifluorescein as a chemical sensing species;

FIG. 4B is a sensor comprising bovine serum albumin as a chemical sensing species;

FIG. 4C is a sensor comprising antifluorescein without sodium azide as a chemical sensing species;

FIG. 4D is a sensor comprising sodium azide as a chemical sensing species;

FIG. 6A is the actual observed results;

FIG. 6B is the corrected response profile;

FIG. 9A is an illustration of an actual photograph at IOOX magnification of a spin casted sol-gel film, FIG. 9B is an illustration of an actual photograph at IOOOX magnification of FIG. 9A at box 9B—9B;

FIG. 9C is an illustration of an actual photograph at lOOX magnification of an aerosol-generated sol-gel film;

FIG. 9D is an illustration of an actual photograph at IOOOX magnification of FIG. 9A at box 9D—9D;

FIG. 10A is an illustration of an actual photograph at 100× magnification of a spin casted sol-gel film;

FIG. 10B is an illustration of an actual photograph at 100× magnification of FIG. 10A at box 10B—10B;

FIG. 10C is an illustration of an actual photograph at 100× magnification of an aerosol generated sol-gel film;

FIG. 10D is an illustration of an actual photograph at 1000× magnification of FIG. 10C at box 10D—10D;

FIG. 11A is an aerosol-generated film of TEOS:water having a molar ratio of 1:2;

FIG. 11B is a spin cast film of TEOS:water having a molar ratio of 1:2;

FIG. 11C is an aerosol-generated film of TEOS:water having a molar ratio of 1:4;

FIG. 11D is a spin cast filmof TEOS:water having a molar ratio of 1:4;

FIG. 12A is an aerosol-generated film of TrEOS-$C_8$;

FIG. 12B is a spin cast film of TrEOS-$C_8$;

FIG. 12C is an aerosol-generated film of TrEOS-$C_8$ and TEOS

FIG. 12D is a spin cast film of TrEOS-$C_8$ and TEOS;

FIG. 13A is emission spectra of rhodamine 6G in an aerosol-generated film;

FIG. 13B is emission spectra of rhodamine 6G in a spin cast film

FIG. 13C is emission spectra of fluorescein in an aerosol-generated film;

FIG. 13D is emission spectra of fluorescein in a spin cast film;

FIG. 13E is emission spectra of pyrene in an aerosol-generated film;

FIG. 13F is emission spectra of pyrene in a spin cast film;

FIG. 14A is an aerosol-generated film on quartz substrate;

FIG. 14B is a spin cast sol-gel film on quartz substrate; and

FIG. 14C is a dip-cast film on the distal end of an optical fiber.

DESCRIPTION OF THE PREFERRED EMBODIMENT

Figure 3:
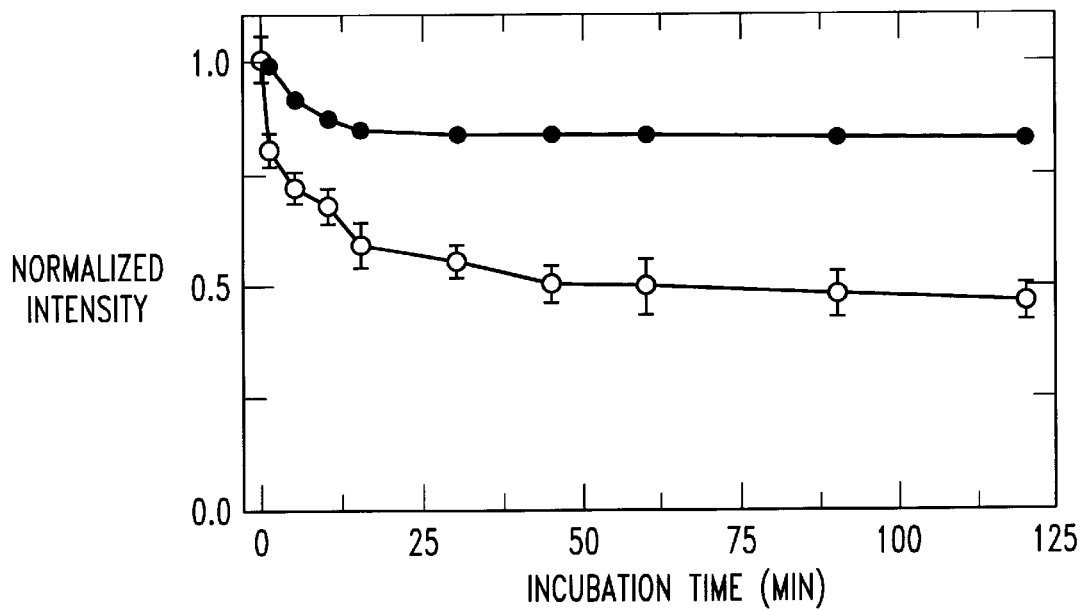
FIG. 3 is a graph of fluorescence intensity vs. incubation time.

A sensor 10 is illustrated in FIG. 1 comprising a substrate 12, like borosilicate microscope slides or quartz glass, a bottom sol-gel layer 16, an immobilized chemical sensing species 18, and a top sol-gel layer 20. Collectively, the bottom sol-gel layer 16 and top sol-gel layer 20 are "Films 14," which is shown in the other figures. Chemical sensing species 18 is selected based on its ability to bind with a particular analyte desired to be detected and is selected from the group consisting of chemical, inorganic and organic recognition elements, such as polyclonal antifluorescein antibody ("AF"), rhodaiine 6G, pyrene and fluorescein. In this particular specification to make it read easier, we have designated 5-(-and 6-)-carboxy-4',5'-dimethylfluorescein ("$Me_2F$") as an example of an analyte and AF as an example of a chemical sensing species 18. In no manner should it be understood that the subject invention works only with this analyte and this chemical sensing species. Maintaining the chemical sensing species 18 affinity and intrinsic function over time is accomplished by entrapping the species 18 within a sandwich of sol-gel films 14 wherein at least the top layer 20 is a thin layer.

The aerosol-based sol-gel composition comprises a sol-gel precursor, a low boiling point alcohol and a diluted acid. A representative sample of sol-gel precursors include tetraethylorthosilicate("TEOS"), an organically modified silane ("ORMOSIL") and N-octyltriethoxysilane ("TrEOS-$C_8$") In one embodiment of this invention, the sol-gel stock solution was prepared with tetraethylorthosilicate ("TEOS"), ethanol, water and hydrochloric acid in the molar ratios between 1:2:2:$10^{-5}$ and 1:2:4:$10^{-5}$. The stock solution is prepared by adding the TEOS and the ethanol to a flask and stirring for about a minute. The water and acid are then added dropwise into the flask under constant stirring and room temperature. The flask is then sealed with parafilm and the stock solution is stirred under ambient conditions (21° C.) for 24 hours.

Once the stock solution is prepared, the aerosol-based sol-gel composition is prepared. This composition is prepared in an aerosol generating instrument 22 as illustrated in one embodiment shown in FIG. 2. The instrument 22 comprises an ultrasonic nebulizer apparatus 24 and a flask 26 having a carrier gas intake 28, a film stopper 30, and a discharging unit 32. Film stopper 30, for example poly (tetrafluoroethylene cohexafluoropropylene, is affixed over the mouth of flask 26 using a glass fitting 34 and a clamp 36. Flask 26 is then inverted and mounted such that film stopper 30 is approximately one centimeter above apparatus 24. The stock solution is then introduced into flask 26 through gas intake 28. Gas intake 28, located at the bottom of flask 26, is glass tubing that allows a carrier gas, which can be any type of carrier gas such as nitrogen, to flow into flask 26. Once the stock solution is within flask 26, apparatus 24 is engaged. In operation, apparatus 24, for example a Holmes ultrasonic humidifier model HM-460B, forms a visible mist of sol-gel material within flask 26 prior to initiating the carrier gas. The apparatus 24 resonates at the frequency of apparatus 24, in this embodiment at about 800 kilohertz.

After a few seconds of operating apparatus 24, the carrier gas is initiated at about 0.5 mL/s and the sol-gel aerosol is transported to substrate 12 through discharging unit 32 at ambient temperatures. Discharging unit 32 comprises Tygon tubing interconnected to a pipette. The entire sol-gel aerosol within instrument 22 is sprayed at the same time which conserves the molecular structure when deposited as a thin film (0.15±0.05 microns). Moreover, this aerosol-generated sol-gel film is capable of increasing the surface area to 100 m2/g to 1000 m2/g by controlling the sol-gel processing chemistry.

In an alternative embodiment of the present invention, in certain instances the film deposition process is repeated upon substrate 12 after waiting at least 5 seconds. Under this particular multilayer scheme, the lower films 14 may or may not fully dry between subsequent deposition steps. The repeated film deposition process may encapsulate other chemical sensing species than the lower films 14.

In yet another alternative embodiment of the present invention, aerosol generating instrument 22 may comprise a compressed air device, like a Badger Airbrush Model 150-4PK. The device contains the sol-gel stock solution. The compressed air from the device is then released which carries the sol-gel stock solution to the device's discharging unit. Once the sol-gel stock solution is discharged from the device's discharging unit, the sol-gel stock solution is converted into an aerosol-generated sol-gel that is applied to substrate 12 at ambient temperatures.

Example. Sample AF-doped films 14 were prepared by first applying a bottom sol-gel film 16 to substrate 12, in this case a glass slide. These bottom sol-gel films 16 were then heated at 40° C. for about 12 h and allowed to cool prior to chemical sensing species 18 application. A 15 µL aliquot of the AF stock solution 16 (50 nM) was deposited on the lower sol-gel film 14 in a 4×4 array (≈1 µL/drop) in order to increase the rate of solvent evaporation. Following evaporation of the solvent buffer, a top sol-gel thin film 18 was applied using the aerosol methodology. All sensors were initially stored dry at 4° C. After 24 h each film was placed in 0.10 M pH 8 phosphate buffer (PB) and stored in PB (4° C.) throughout the experiments.

In order to determine the performance of the films 14, the following experiment was conducted. A $Me_2F$ stock solution was prepared such that the number of moles of $Me_2F$ present in 3 mL was twice the number of moles of AF in a given sandwich film (there is a 2:1 binding of hapten of $Me_2F$ to antibody AF). The fluorescence spectrum of this 3 mL solution was then collected in triplicate ($\lambda_{ex}$=476±4 nm) using a monochromator (16 nm bandpass) and a 495 nm longpass filter. Once these spectra were acquired, an AF-doped film was introduced into this stirred solution ($t_0$) such that the film was maintained well below the beam path. The $Me_2F$ emission spectra Were then recorded (495–650 nm) as a function of incubation time. The area under these time-dependent emission spectra, between 500 and 545 mn, was integrated in order to generate the intensity vs. incubation time profiles as shown in FIG. 3.

The use of sol-gel-derived matrices as platforms for chemical, immunological and biosensing is predicated on the chemical sensing species 18 (i.e., dopant) remaining entrapped within sensor 10. Leaching of the chemical sensing species 18 can severely compromise sensor performance, particularly in situations where continuous monitoring is required. Leaching of an entrapped chemical sensing species 18 is typically probed by testing the supernatant for dopant material. Steady-state fluorescence anisotropy of the $Me_2F$ incubation solution was used to investigate antifluorescein (AF) leaching from the thin, aerosol-generated sol-gel-derived film. In the current system, the rotational diffusion of fluorophores is a dominant cause of fluorescence depolarization. Therefore, for a solution of constant viscosity, the measured steady-state fluorescence anisotropy (<r>) is directly proportional to the volume of the rotating unit. For our system, consisting of an antibody, AF, and its fluorescent hapten, $Me_2F$, which differ in size by more than an order of magnitude, anisotropy measurements provide a convenient means to determine the identity of the fluorescent analytes in solution. Specifically, this technique allows one to differentiate between free $Me_2F$ and the $Me_2F$-AF complex; providing a convenient tool to follow chemical sensing species 18 leaching from sensor 10.

Steady-state anisotropy experiments showed that a substantial population of AF leached from the sol-gel film matrix of sensor 10. To begin and address the origin of this problem, optical microscopy was used. It is well known that phosphate can catalyze the condensation reaction of the sol-gel process, resulting in cracking due to large capilary forces within the matrix. Thus, separate sensors 10 were prepared with the same quantity of bovine serum albumin ("BSA") (135A) replacing the AF which has phosphate in a buffer solution. BSA was chosen because, like AF, it too is a large (MW=67000), multidomain protein. Optical micrographs of these films 14 are shown in FIG. 4. The BSA-doped film (FIG. 4B) is transparent and crack free, while the AF-doped film (FIGS. 4A–D) exhibited many large cracks 38, which ultimately allowed the antibody, AF, to leach from the sensor matrix. Together these results suggested that phosphate was not the culprit.

Figure 4A:
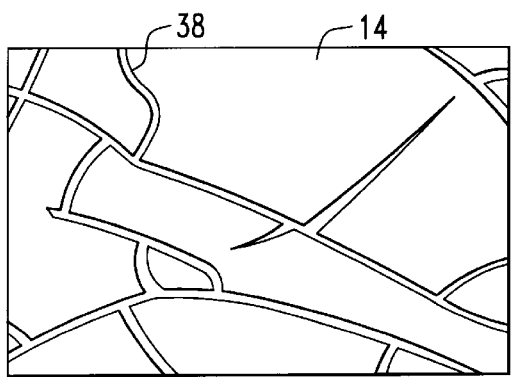
FIGS. 4A–D are schematics of four microphotographs of several sol-gel derived sensing platforms having different chemical sensing species.
Figure 4B:
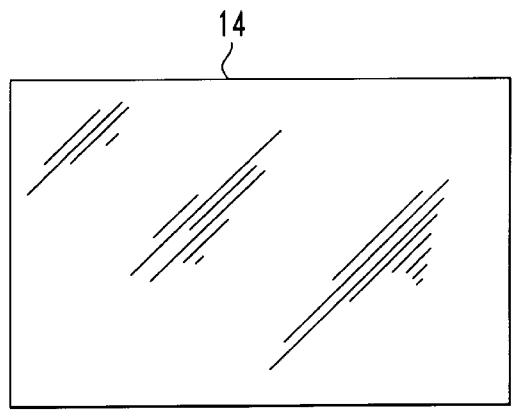
Figure 4C:
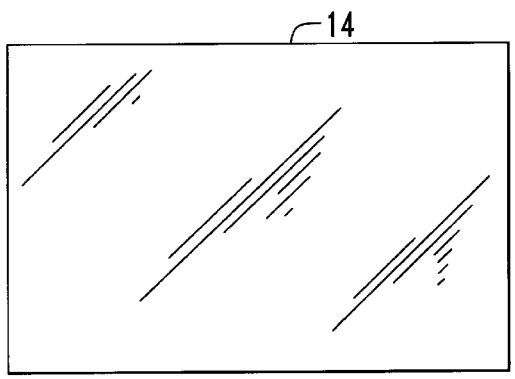
Figure 4D:
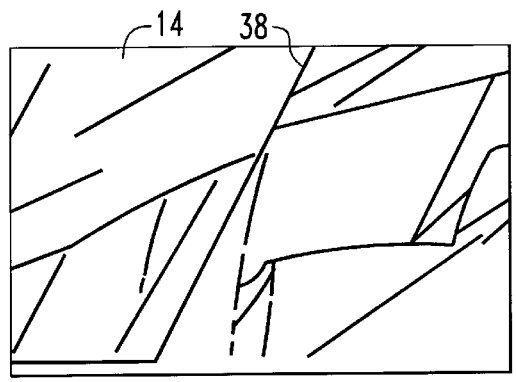

Careful checking revealed that the AF stock solution contained the preservative sodium azide (2 mM) whereas the BSA samples had no such preservative added. On removing the azide (FIG. 4C) from the AF stock solution the films 14 were uncracked. Unfortunately, dialysis was used to remove the azide and it is possible that other small dissolved agents, that too could be removed by dialysis, might have contributed to the cracking process. To prove that azide was indeed the crack producing agent, we prepared a series of sandwich films 14 exactly as described above but used 15 µL of 2 mM sodium azide in place of the AF. These films 14 (FIG. 4D) exhibited the same high degree of cracking 38 observed when the azide was present in the AF solution (FIG. 4A). Together these results show that it was indeed azide which adversely affected the sol-gel film morphology. All subsequent sensors 10 were prepared using the AF solution without the azide preservative.

After solving the film cracking problem, an investigation of whether the AF molecules entrapped within the aerosol-generated sol-gel-derived thin film maintained its ability to bind $Me_2F$. Toward this end, the fluorescence from a $Me_2F$ solution was monitored as it was incubated with an AF-doped sandwich film of a sensor 10. If the entrapped AF were active and accessible, $Me_2F$ from the bulk solution would diffuse into the sol-gel thin film and become bound by the AF. However, because the test solutions contained exactly twice as many moles of $Me_2F$ as entrapped AF, if all of the sol-gel sandwiched AF were viable and accessible, the $Me_2F$ fluorescence would drop to zero as all available $Me_2F$ became AF bound. FIG. 3 presents typical fluorescence intensity vs. incubation time profiles for the sol-gel-derived AF sandwich films 14 aged two (2) and thirty-four (34) days.

In both cases, there is an initial decrease in intensity and a leveling off at a non-zero value. Further, 2 day-old films 14 (○) exhibit greater overall response when compared to the 34 day-old preparation (●).

Prior to analysis of the intensity vs. incubation time profiles, there was an investigation whether any antibody leached from the film, the fluorescent hapten was photostable, and there was any non-specific adsorption of the $Me_2F$ to the sol-gel composition. That is, the observed decrease in the $Me_2F$ fluorescence as a function of incubation time (FIG. 3) could result from: (1) $Me_2F$ diffusing into the sol-gel matrix and binding to the entrapped AF; (2) AF leaching from the sol-gel thin film; (3) photobleaching, and/or (4) physisorption of the $Me_2F$ to the sol-gel composite. To discriminate between these possible scenarios, blank films 14 (i.e., containing no AF) and steady-state anisotropy were used.

Figure 5:
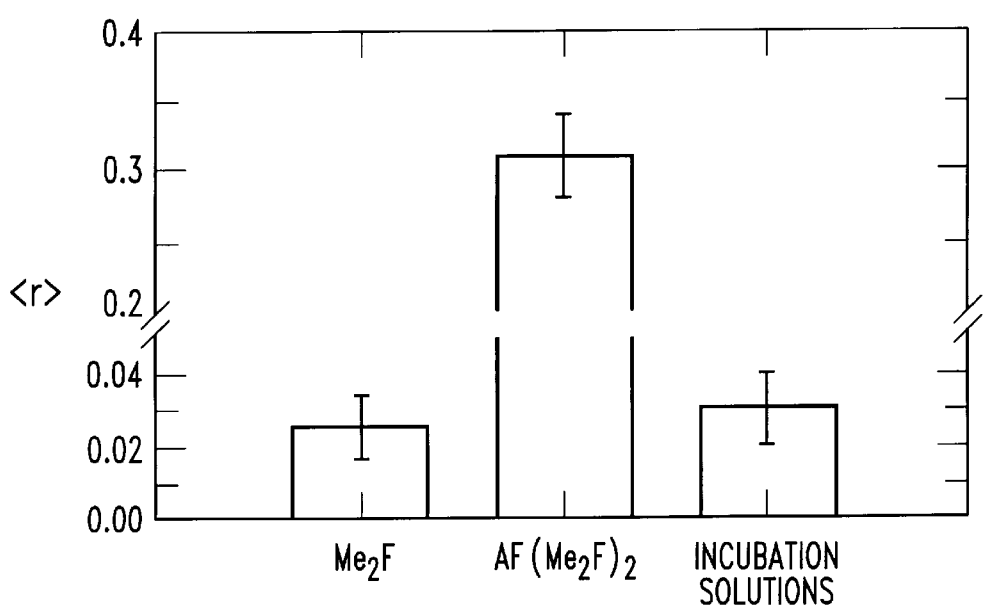
FIG. 5 is a graph of steady-state fluorescene anisotropy of free $Me_2F$, $Me_2F$-AF complex, and the incubation solution following a response experiment.

When $Me_2F$ solutions were subjected to blank sol-gel sandwich films 14, there was no detectable decrease in the $Me_2F$ fluorescence, eliminating photobleaching and non-specific physisorption as possible causes of the results seen in FIG. 3. FIG. 5 shows the average fluorescence anisotropy (<r>) for free $Me_2F$, $Me_2F$ complexes with AF ([AF]>2 [$Me_2F$]), and the incubation solutions following a typical response experiments. These data clearly indicate that only free $Me_2F$ remains in the incubation solution following an experiment, thereby eliminating antibody leaching, and confirming that $Me_2F$ is diffusing into the sol-gel sandwich film architecture and binds to a subpopulation of the entrapped AF. Similar results were observed for all AF-doped films 14 at every experimental storage time.

Given the fact that the sandwich films 14 indeed bind selectively to $Me_2F$ in the sensor 10, the next issue centers on the fact that not all of the $Me_2F$ is bound by the AF (i.e., the signal does not drop to zero). This suggests that after two days of storage, only 50% of the AF entrapped between the sol-gel thin films 14 is accessible and/or able to bind $Me_2F$. Thus, this decrease to a non-zero value could be a manifestation of AF instability within the sol-gel composite and/or the entrapment process rendering a certain subpopulation of antibody inaccessible.

Figure 6A:
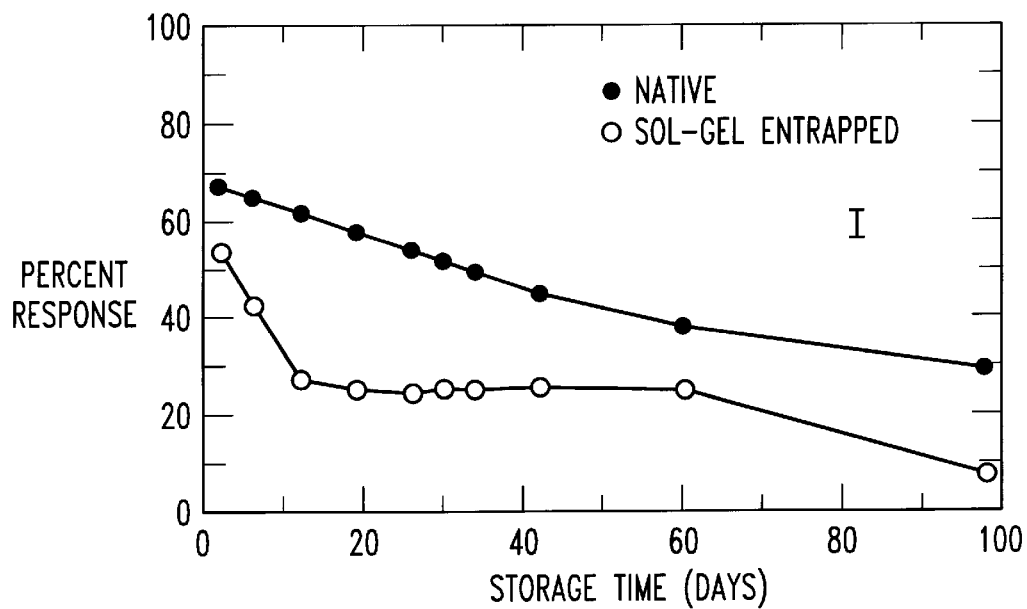
FIGS. 6A–B are graphs of effects of storage time on analytical response.
Figure 6B:
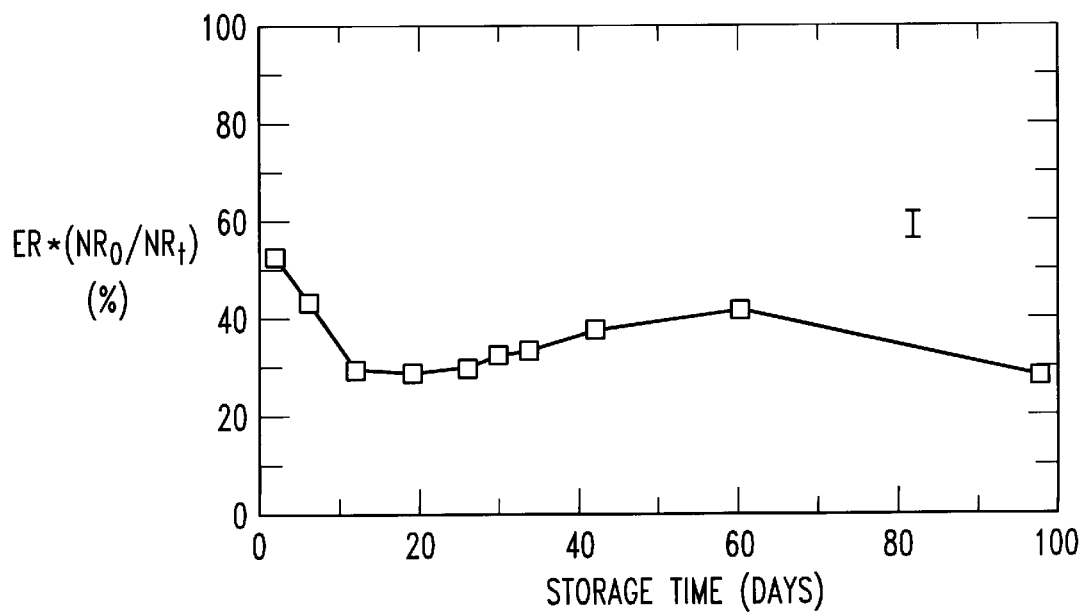

To begin to address these issues we determined the response of the films 14 as a function of storage time as outlined above and the results are summarized in FIG. 6A (○). For comparison purposes we also show the response for native AF in the absence of the azide preservative (●). Together these results illustrate two key points. First, the native AF (without the azide) is intrinsically unstable. Second, the sol-gel entrapped AF too is unstable with time. In an effort to compensate for the inherent instability of the native antibody, the observed experimental response (○, ER) data are normalized by multiplying by a scaling factor (the initial native AF response $NR_O$) divided by the native AF response at the experimental time t ($NR_t$)). The results of this compensation process are shown in FIG. 6B. These results indicate that about 50% of the entrapped AF is accessible to $Me_2F$ initially, and this value decreases during the first two weeks following entrapment. However, after two weeks, the response of the sol-gel-entrapped AF levels off, and increases slightly over the next seven weeks, prior to decreasing to approximately 30% after 98 days of storage. This data indicates that in the absence of the azide preservative, less than half of the AF antibodies entrapped within the sol-gel thin film initially (day 0) remain viable even in the native situation after 98 days of storage. Given this fact, the maximum possible response for these sol-gel-derived sandwich films 14 stored 98 days would be 50% (i.e., $NR_{98}=\frac{1}{2} NR_O$). The actual 8% response observed for the 98 day-old sensor 10 demonstrates that other factors such as AF accessibility and/or mobility within the composite are contributing to the diminishing response. The origin of the observed response decrease was investigated further by determining the effects of storage time on the response times for the AF-doped films 14.

Figure 7:
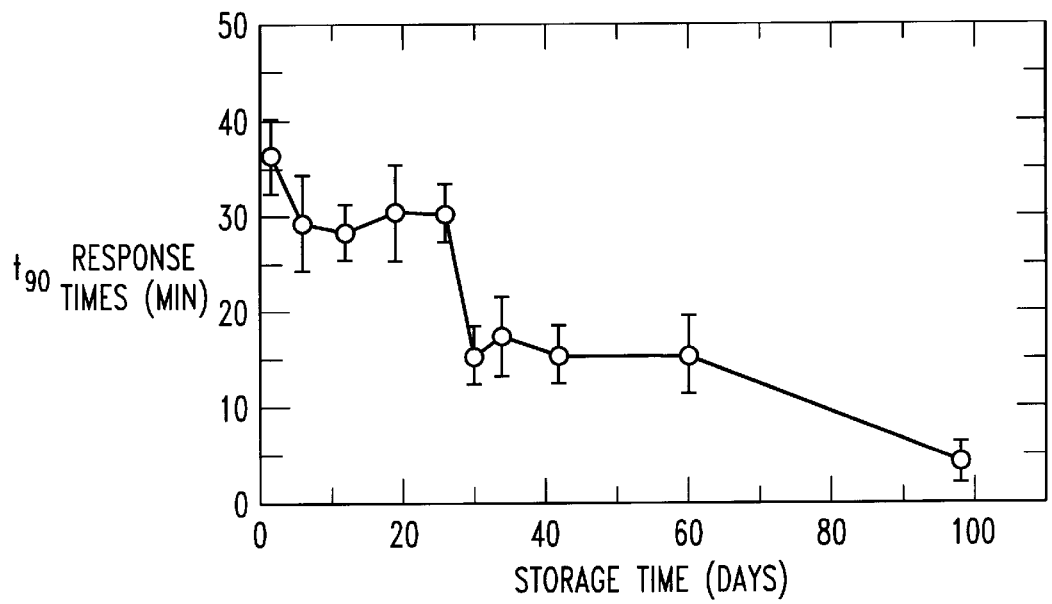
FIG. 7 is a graph of response times of AF-doped sol-gel sensors as a function of storage time.

The response time is defined as the time required to reach 90% of the total observed response ($t_{90}$). FIG. 7 summarizes the response times of each AF-doped sensor 10 as a function of storage time. These results are intriguing because they show that the response time actually improves as the AF-doped sol-gel-derived films 14 age. We began to explore these results by considering the physical aspects of the sensor 10 architecture (FIG. 1). Recall that in one embodiment of the subject invention, we spray and dry a bottom sol-gel thin film, deposit and dry an AF layer, and overcoat this AF layer with an aerosol-generated top sol-gel film. When this upper sol-gel film impinges on the lower film surface, it is likely that a certain fraction of the total, available AF molecules might become solubilized by the top-sol-gel layer and diffuse toward the upper film/air interface in the time prior to gelation of the upper sol-gel film layer. If this process were to occur, a subpopulation of the AF antibodies could become distributed within the upper sol-gel thin film, resulting in subpopulations of entrapped AF of varying accessibility. Given this scenario, AF entrapped within the upper sol-gel layer (sandwich scheme) is viable and accessible via a long and circuitous path. This would support both maximum response and the relatively slow response time for a fresh film. The decrease in response observed within the first two weeks following entrapment is consistent with a certain subpopulation of entrapped AF no longer able to bind $Me_2F$ or becoming inaccessible due to the continuing polycondensation/networking of the composite. If the subpopulation of AF antibodies, which no longer are able to bind $Me_2F$, were sequestered within the upper film, then this would account for the observed decrease in response time, as only the more accessible AF molecules can bind $Me_2F$. This being the case, one would expect to see a non-exponential decrease in the $Me_2F$ fluorescence as a function of incubation time initially, due to the varying accessibility of subpopulations of entrapped AF. Analysis of the available response vs. incubation time profiles (FIG. 6A) for the AF-doped sandwich films 14 were fit to single and double exponential decay models (results not shown). Interestingly, the results demonstrate that a two-term kinetic model (i.e., $I(t)=g_1 \exp(-k_1 t)+g_2 \exp(-k_2 t)$) is required to adequately describe the fluorescence intensity vs. incubation time response profiles for all films 14 less than 34 days old. After 34 days of storage the intensity vs. incubation time profiles are described by a single exponential decay model. Together these results suggest that, for the first five weeks following entrapment, the response of AF resulted from two (or more) populations of AF which were viable and accessible to hapten. After these five weeks, only the sandwiched AF molecules remain accessible and/or viable.

An important aspect in the development of any sensor is the ability to reset or regenerate the immobilized recognition chemistry. The regenerability of the AF-doped sandwich films 14 was investigated using 4 M NaCl as the chaotropic reagent. This chaotrope was chosen for four reasons: (1) it is one of the more mild chaotropes; (2) the nature of the sol-gel composite prevents using acidic or basic chaotropes, as extremes in pH can alter the film morphology, resulting in a loss of pore structure due to intrapore condensation; (3) it has been used previously to disrupt antibody/hapten complexation, and effectively regenerate a base affinity column; and (4) it is inexpensive, readily available, and does not present a difficult waste disposal problem along with other chaotrope agents.

Figure 8:
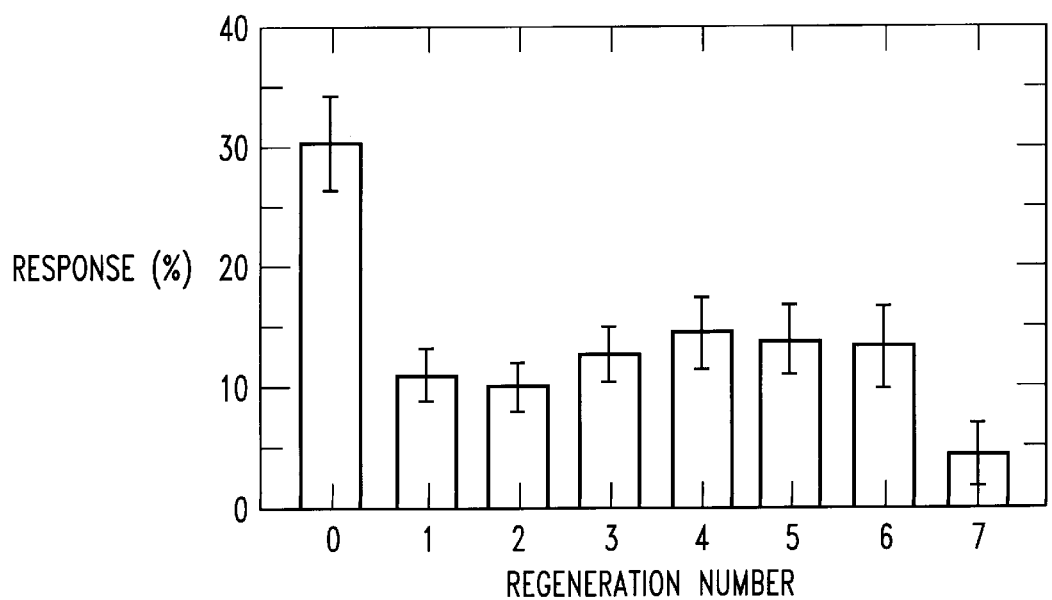
FIG. 8 is a graph of regeneration number of the AF-doped sol-gel sensor response.

This regeneration protocol is as follows. Upon completion of an experimental run in which the response of the sensor was measured (FIG. 4), the film was removed from the $Me_2F$ incubation solution, dipped in water for 2 seconds, and soaked in 4 M NaCl for 2 min. The sensor was then removed, dipped in water and phosphate buffer, and the response experiment repeated. The response vs. number of regeneration cycles data for AF doped films 14 aged 30 days (similar results were obtained for films 14 within the response plateau region of FIG. 6B) is shown in FIG. 8. These results indicate that 40–50% of the initial response can be recovered through six regenerations.

Comparative Examples. The present invention is compared against the conventional spin-casting method of applying thin sol-gel films upon a substrate 12. In spin casting, the substrate was held on a custom built rotor and 200–300 μL of the appropriate (neat or fluorophore-doped) sol-gel solution was pipetted directly onto the substrate. The substrate was rotated at 2000 rpm for 15 s to form the film. Films were dried and aged (at 20–22° C.) for 1–3 weeks.

Figure 9A:
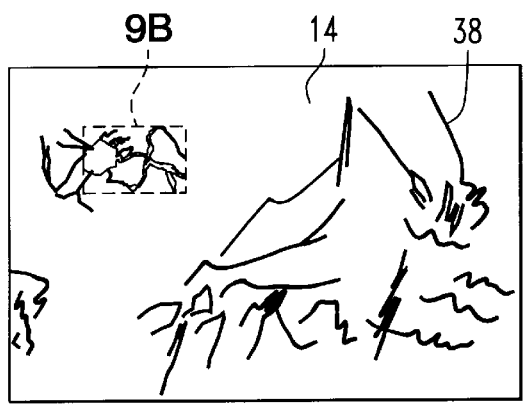
FIGS. 9A–D are comparisons of spin cast and aerosol generated sol-gel films comprising TEOS on a substrate.
Figure 9B:
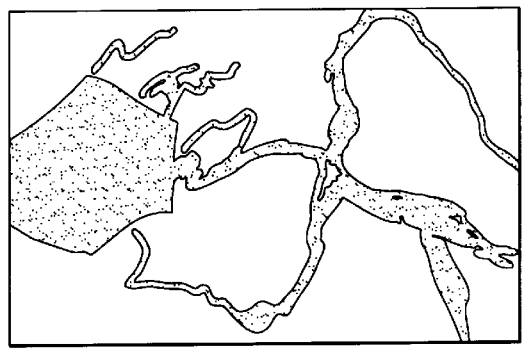
Figure 9C:
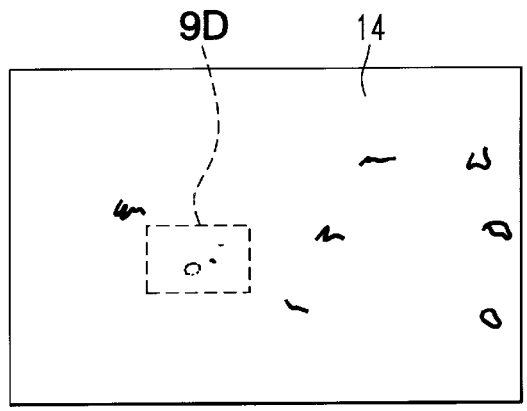
Figure 9D:
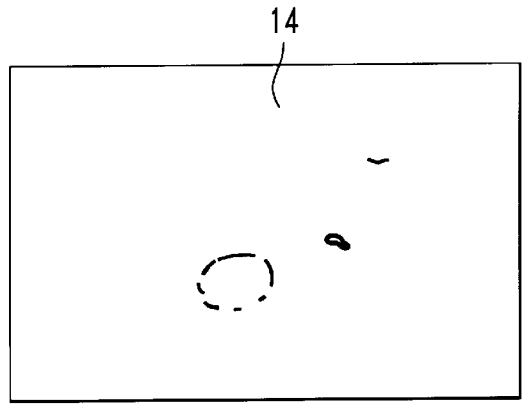
Figure 10A:
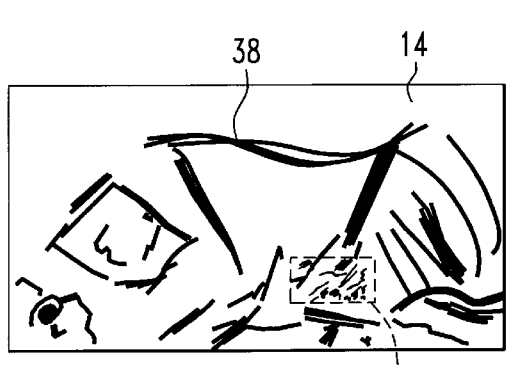
FIGS. 10A–D are comparisons of spin cast and aerosol generated sol-gel films comprising TrEOS-$C_8$ on a substrate.
Figure 10B:
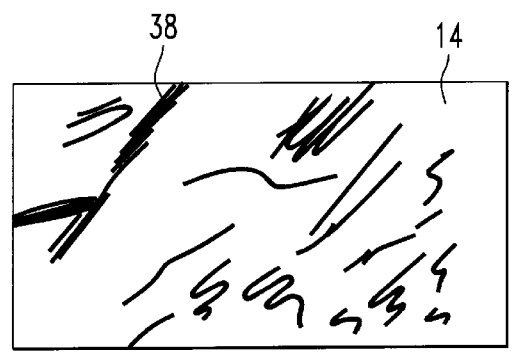
Figure 10C:
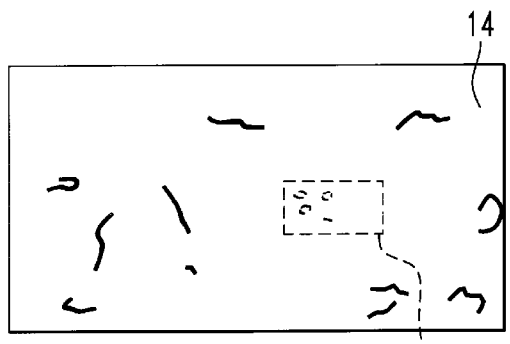
Figure 10D:
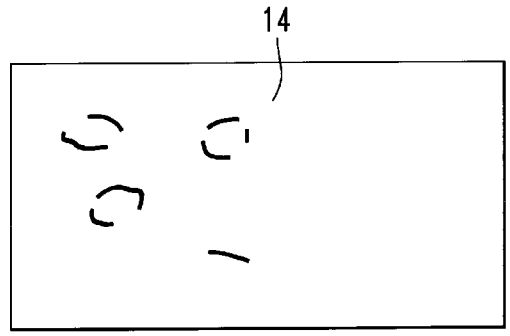

FIGS. 9A–D and 10A–D present typical Scanning Electron Microscopy ("SEM") images of TEOS- and TrEOS-$C_8$-derived sol-gel thin films, respectively. The upper image within each panel pair corresponds to 100× magnification, while the lower panel pair image represents 1000× magnification of the area within the highlighted box shown in the upper image. In particular, FIGS. 9A and 10A are illustrations of actual photographs at 100× magnification of a spin casted sol-gel film. And FIG. 9B and 10B are illustrations of actual photograph at 1000× magnification of FIGS. 9A at box 9B—9B and 10A at box 10B—10B. In contrast, FIGS. 9C and 10C are illustrations of actual photographs at 100× magnification of an aerosol-generated sol-gel film. While FIGS. 9D and 10D are illustrations of actual photographs at 1000× magnification of FIGS. 9C at box 9D—9D and 10C at box 10D—10D. These SEM images illustrate several key points. First, the aerosol deposition method yielded uniform, uncracked thin TEOS-derived films. Second, TEOS films produced from the same sol-gel stock solution, using the conventional spin coating approach, exhibited a high degree of cracking 38 (compare FIGS. 9A and 9B to 9C and 9D). Third, conventional spin casting yielded highly rippled TrEOS-$C_8$-derived films (FIG. 10A) that also contained cracks 38. Fourth, the aerosol technique yielded reasonably uniform TrEOS-$C_8$-derived sol-gel thin film (FIG. 10C), containing the organic ($C_8$) ligand. Finally, TrEOS-$C_8$-based samples were, however, characterized by small (d=6 μm), raised, circular domains (blisters) dispersed randomly within the uncracked film base.

Prior to comparing films prepared with TEOS:water molar ratios of 1:2 and 1:4, it is prudent to review the effects of alkoxide/water molar ratio on the chemistry of the sol-gel process. The alkoxide/water molar ratio influences the properties of the final sol-gel composite in at least three ways. (1) Promotion of alkoxide hydrolysis. (2) For alkoxide/water molar ratios greater than $\frac{1}{4}$, the alcohol producing condensation reaction is favored, while the water forming condensation reaction is favored when the molar alkoxide/water ratio is less than $\frac{1}{4}$. (3) Excess water (above that needed for complete hydrolysis of all alkoxide residues) also promotes hydrolytic depolymerization (i.e., the reverse of the water condensation reaction). The latter point is apparently important when one compares the SEM images of aerosol-generated sol-gel films prepared with alkoxide:water molar ratios of 1:2 and 1:4. Aerosol deposition of the TEOS films were similar in many regards; however, the films prepared with a TEOS/water molar ratio of 1:4 always exhibited a greater fraction of particulates. These particulates are likely associated with the aforementioned hydrolytic depolymerization process.

Film thicknesses were measured for triplicate TEOS and TrEOS-$C_8$-derived samples (Table 1). The TEOS:water and TrEOS-$C_8$:water molar ratios were 1:2 and 1:3, respectively. TEOS-based films produced using the aerosol deposition scheme (Table 1, "one application") were 0.62±0.05 μm thick. Films produced using five successive applications (5 s between coatings) (Table 1, "five applications") were 2.0±0.02 μm thick. SEM images of these more thick films (data not shown) were indistinguishable from those presented in FIG. 10C. This result demonstrates that thick uncracked films can be quickly formed using successive aerosol applications. The film thickness uniformity increases with the number of aerosol coatings. The aerosol-deposition scheme also provides an attractive means to produce uniform sol-gel-derived films with tunable thicknesses. Spin coating of the same TEOS sol-gel solutions always resulted in the formation of 2.0±0.10 μm thick films that were cracked. Thus, the subject invention's multistep aerosol-deposition scheme generates films as thick as those produced in a single spin coating run without cracks, of significantly greater uniformity, and good optical quality.

The deposition scheme used also affects the thickness and morphology of the TrEOS-$C_8$-derived films. Aerosol-generated TrEOS-$C_8$ films produced by a single application were 0.70± 0.08 μm thick, while spin coating yielded films that were 2.0±0.15 μm thick. SEM images (FIG. 10C) revealed a few blisters on the aerosol-generated TrEOS-$C_8$ films, while spin coating (FIG. 10A) lead to a highly rippled, heterogeneous surface. The increased heterogeneity in the TrEOS-$C_8$-derived sol-gel films, relative to the TEOS samples, is fully consistent with the profilometry results.

TABLE 1

| Sample | Film Thickness (microns) |
|---|---|
| TEOS (one application by aerosol) | 0.62 ± 0.05 |
| TEOS (five applications by aerosol) | 2.00 ± 0.02 |
| TEOS (spin coating) | 2.00 ± 0.10 |
| TrEOS-C8 (aerosol) | 0.70 ± 0.08 |
| Tr-EOS-C8 (spin coating) | 2.00 ± 0.15 |

In order to minimize surface contamination from adventitious carbon, a series of 2 μm thick films were prepared under argon using the aerosol (5 coats) and spin coating (1 coat) schemes and subjected to Electron Spectroscopy for Chemical Analysis (ESCA). An inert atmosphere sample-transfer vessel was also used to transport the films from the glove bag directly to the ESCA instrument's high-vacuum environment. Take-off angles (angle between the surface plane and the detector) of 15, 45, and 80° were used to control the ESCA sampling depth. Table 2.1 provides estimated sampling depths for the C (1s), O (1s), and Si (2p) photoelectrons.

TABLE 2.1

| Element | Estimated Sampling Depths (Å) | | |
|---|---|---|---|
| (Photoelectron) | 15° | 45° | 80° |
| C (1s) | 12 | 33 | 46 |
| O (1s) | 10 | 28 | 40 |
| Si (2p) | 13 | 36 | 50 |

TABLE 2.2

| Take-off Angle | TEOS (aerosol) | | | TEOS (spin coated) | | |
|---|---|---|---|---|---|---|
| (degrees) | % C | % O | % Si | % C | % O | % Si |
| 15 | 33.5 ± 0.1 | 49.1 ± 0.05 | 17.5 ± 0.05 | 28.1 ± 0.05 | 53.3 ± 0.02 | 18.6 ± 0.05 |
| 45 | 38.6 ± 0.2 | 52.5 ± 0.2 | 18.9 ± 0.02 | 22.6 ± 0.6 | 56.9 ± 0.5 | 20.6 ± 0.1 |
| 80 | 27.8 ± 0.7 | 53.1 ± 0.5 | 19.1 ± 0.2 | 19.9 ± 0.8 | 58.9 ± 0.7 | 21.2 ± 0.08 |

TABLE 2.3

| Take-off Angle | TrEOS-$C_8$ (aerosol) | | | TrEOS-$C_8$ (spin coated) | | |
|---|---|---|---|---|---|---|
| (degrees) | % C | % O | % Si | % C | % O | % Si |
| 15 | 66.3 ± 0.8 | 23.4 ± 0.9 | 10.3 ± 0.03 | 78.1 ± 0.03 | 14.0 ± 0.03 | 7.88 ± 0.02 |
| 45 | 45.9 ± 0.03 | 38.7 ± 0.2 | 15.4 ± 0.3 | 73.1 ± 0.3 | 18.1 ± 0.3 | 8.78 ± 0.05 |
| 80 | 41.7 ± 3 | 42.0 ± 2 | 16.4 ± 0.7 | 73.6 ± 0.1 | 17.5 ± 0.1 | 8.91 ± 0.01 |

The aerosol and spin cast films for these comparative examples shown in tables 2.2 and 2.3 were prepared from the same sol-gel stock solution at essentially the same time. The aerosol (as shown in FIG. 2) and spin coating apparatuses were also contained within the same inert atmosphere environment. Thus, film differences should not result from differences in the sol-gel solution and/or deposition environment.

Table 2.2 also collects the elemental surface analytical data for TEOS-derived films produced using the aerosol and spin coating schemes (molar TEOS:water=1:2). In an ideal case a completely hydrolyzed TEOS-based sol-gel composite, free of adsorbed carbon contaminants, would exhibit no detectable carbon signal. ESCA spectra for all our TEOS films reveal that carbon is always present at the surface, and the % C decreases as the sampling depth increases. Further, approximately 6% more carbon is observed at all sampling depth for the aerosol-generated films relative to the spin cast films.

Carbon present on the surface of the TEOS-derived samples is consistent with the presence of residual ethoxy units associated with incomplete hydrolysis of the metal alkoxide precursor during sol-gel processing. However, the difference between % C on the surface (top 12 Å) of the aerosol-generated (34%) and spin-cast (28%) films suggests that structural features within the final sol-gel films can be manipulated by the choice of deposition method. Specifically, these results suggest that the extent of ethoxide hydrolysis is lower within the aerosol-derived films compared to those produced by spin coating. Also, a more carbon rich 10–50 Å top surface can be produced using TEOS and the aerosol deposition scheme. Such control of the concentration of carbon-containing species provide the opportunity to control the hydrophilicity and hydrophobicity characteristics of the films 14.

Table 2.3 also summarizes the ESCA data for TrEOS-$C_8$-derived films produced using the aerosol and spin coating schemes (molar TrEOS-$C_8$:water=1:3). These results illustrate several interesting points. First, the % C present in the TrEOS-C,-derived films is as expected significantly higher compared to the TEOS films. Second, the films produced using the spin coating scheme exhibit higher % C values for all sampling depths relative to the aerosol produced films. Third, carbon appears more uniformly distributed (over a 10–50 Å sampling depth) within the spin coated TrEOS-$C_8$-derived films, with the % C varying only 5% between the top 10 to 50 Å from the surface. In contrast, the aerosol-generated films exhibited over 25% greater carbon at the surface relative to carbon level detected 50 Å from the surface. Together these data indicate segregation of the organic moiety within ORMOSIL-derived aerosol-generated thin sol-gel film composites and that one can control in some manner the segregation process. In particular, there is a $C_8$ rich region in the top most layer, not entirely but possibly due to segregated $C_8$ hydrocarbon chains in the outer most layer. Interfacial tunability is an attractive future of the ORMOSIL-based system especially when used as a stationary phase for open-tubular liquid chromatography.

ESCA revealed that greater carbon levels were present at the surface of the TrEOS-$C_8$ spin-cast films relative to the aerosol-generated specimens. These results are intriguing, given that the films were prepared from the exact same stock sol-gel solution within the exact same environment. To more completely investigate the nature of this difference, diffuse-reflectance infrared Fourier-transform spectroscopy (DRIFTS) was used. DRIFTS qualitatively compares the bulk carbon concentration within TrEOS-$C_8$ films produced from the aerosol or spin coating schemes by following the symmetric and antisymmetric fundamental stretching vibrations of the ORMOSIL alkyl residues (e.g., $CH_2$ and $CH_3$) at 2850–2960 $cm^{-1}$ (FIGS. 11A–D and 12A–D).

Figure 11A:
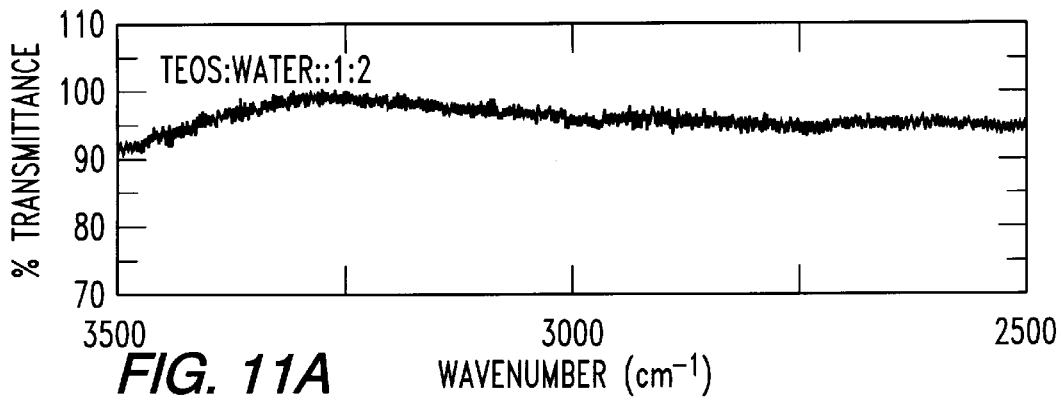
FIGS. 11A–D are diffuse-reflectance FT-IR spectra of films comprising TEOS and water with different molar ratios.
Figure 11B:
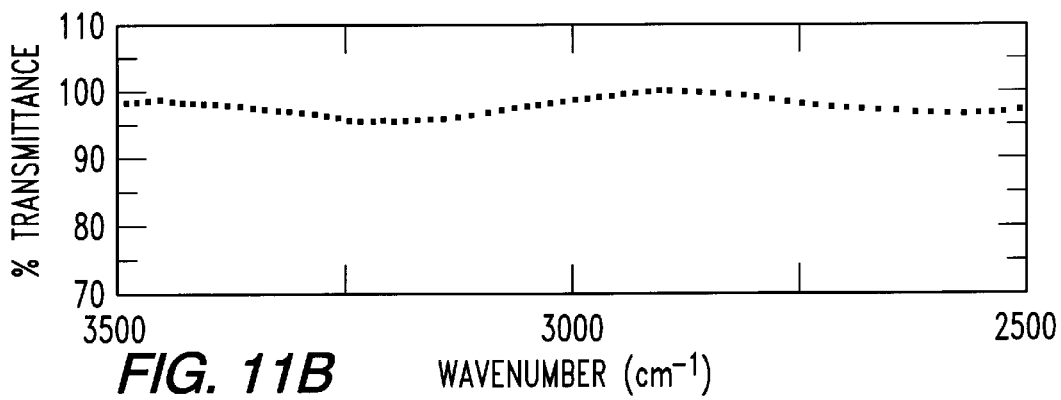
Figure 11C:
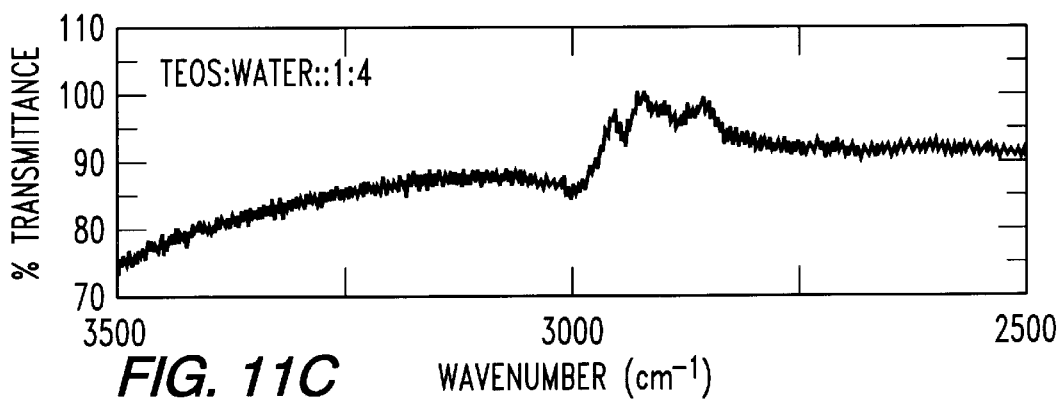
Figure 11D:
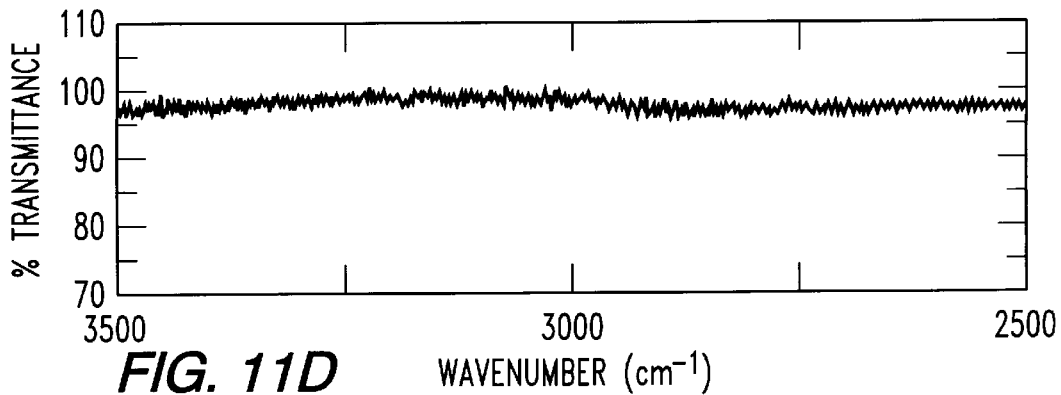

FIGS. 11A–D present typical DRIFTS spectra for aerosol-generated (solid line) and spin cast (dotted line) TEOS-derived sol-gel thin films prepared with TEOS:water molar ratios of 1:2 (FIG. 11A for aerosol generated films and 11B for spin cast films) and 1:4 (FIGS. 11C for aerosol generated films and 11D for spin cast films). For the 1:2 films (FIGS. 11A and 11B), no absorbance from the C—H stretching mode is observed. This suggests that, within the detection powers of infared ("IR"), hydrolysis within the sol-gel composite bulk has gone to completion, and that unhydrolyzed ethoxy species are not present to significant degree within the bulk sol-gel film (2 μm thick). The IR spectrum for the spin-coated 1:4 film (FIG. 11D) also exhibits this same trend. In contrast, C—H stretch and O—H absorption are clearly evident in the aerosol-generated 1:4 films (FIG. 11C). This is consistent with incomplete hydrolysis, the ESCA results, and the formation of hydrated silica moieties present on the film surface.

Figure 12A:
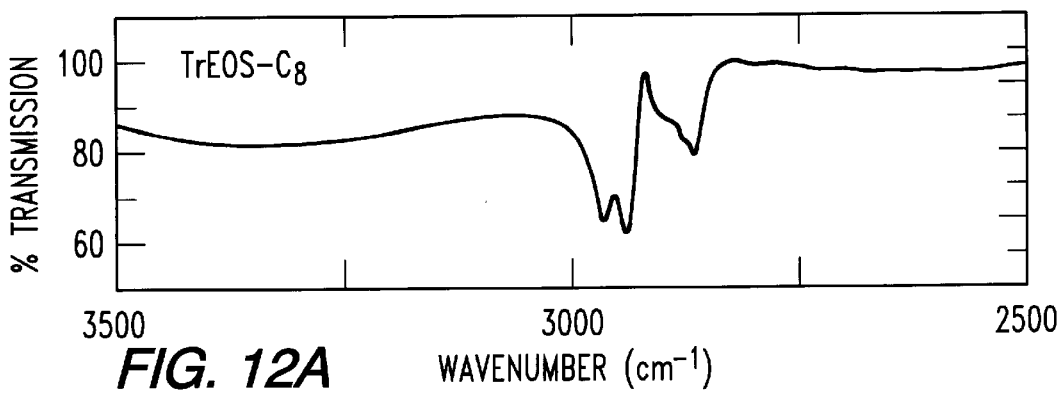
FIGS. 12A–D are diffuse-reflectance FT-IR spectra of films comprising TrEOS-$C_8$.
Figure 12B:
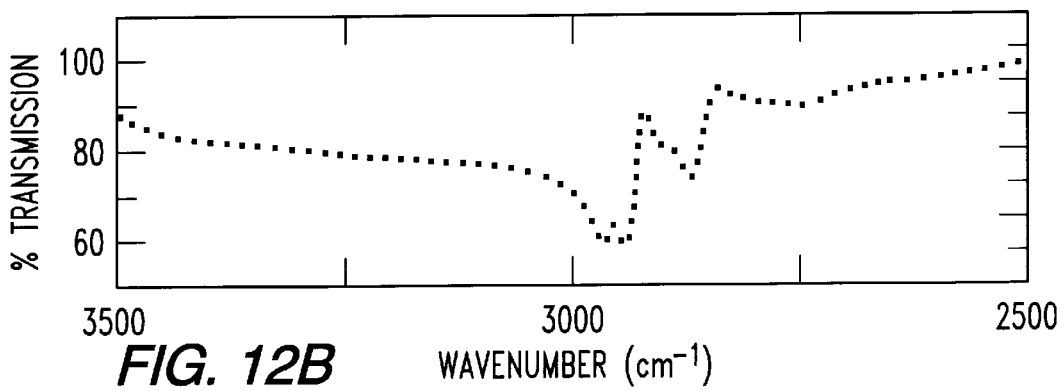
Figure 12C:
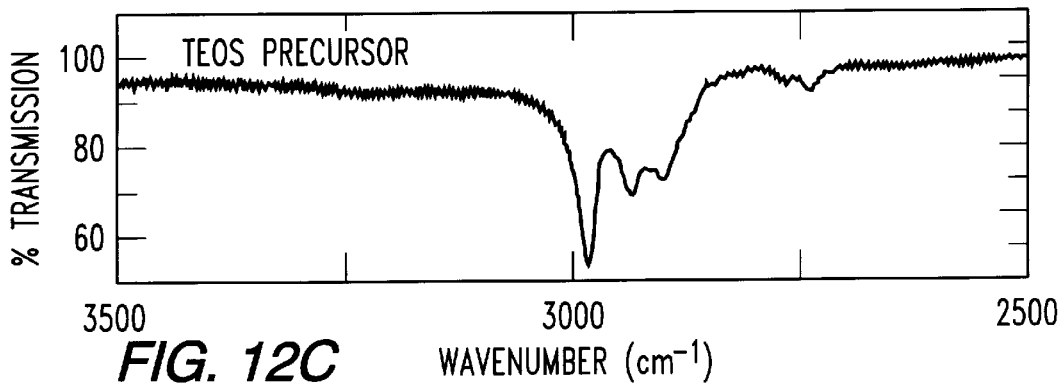
Figure 12D:
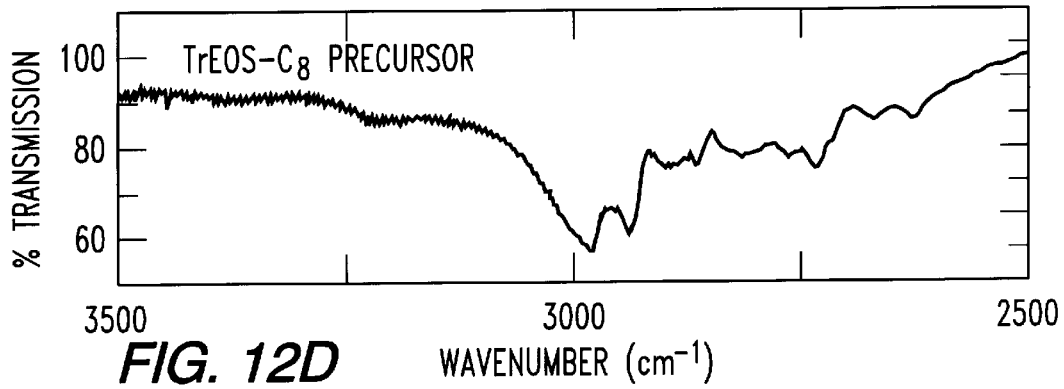

The IR spectra for the TrEOS-$C_8$ films (molar TrEOS-$C_8$:water=1:3) are presented in FIGS. 12A for aerosol generated films and 12B for spin cast films. These data show that the aerosol-generated and spin-cast TrEOS-$C_8$-derived films are very similar (from a bulk standpoint), indicating that the surface segregation of carbon observed in the ESCA experiments is a function of the deposition technique used, and not an anomalous result. For comparison, the IR spectra of neat TEOS and TrEOS-$C_8$ are shown in FIGS. 12C and 12D, respectively.

The local microenvironment surrounding a series of model dopants (rhodamine 6G ("R6G",) fluorescein, and pyrene) was determined by following their steady-state emission spectra. Typical emission spectra for these systems are depicted in FIGS. 13A–F (comparison of aerosol-generated v. spin cast films) where the left hand series of panels correspond to aerosol-generated films and the corresponding spin cast films are shown in the right hand panel series. Shown within each individual panel set are the emission spectra for each dopant/probe in neat liquid ethanol (solid line), the probe adsorbed to the bare substrate (long dash line), and the probe entrapped within films produced from sol-gel solutions with TEOS:ethanol:water:HCl of 1:2:2:$10^{-5}$ (short dash line) and 1:2:4: $10^{-5}$ (dotted line).

Figures 13A, 13B, 13C, 13D:
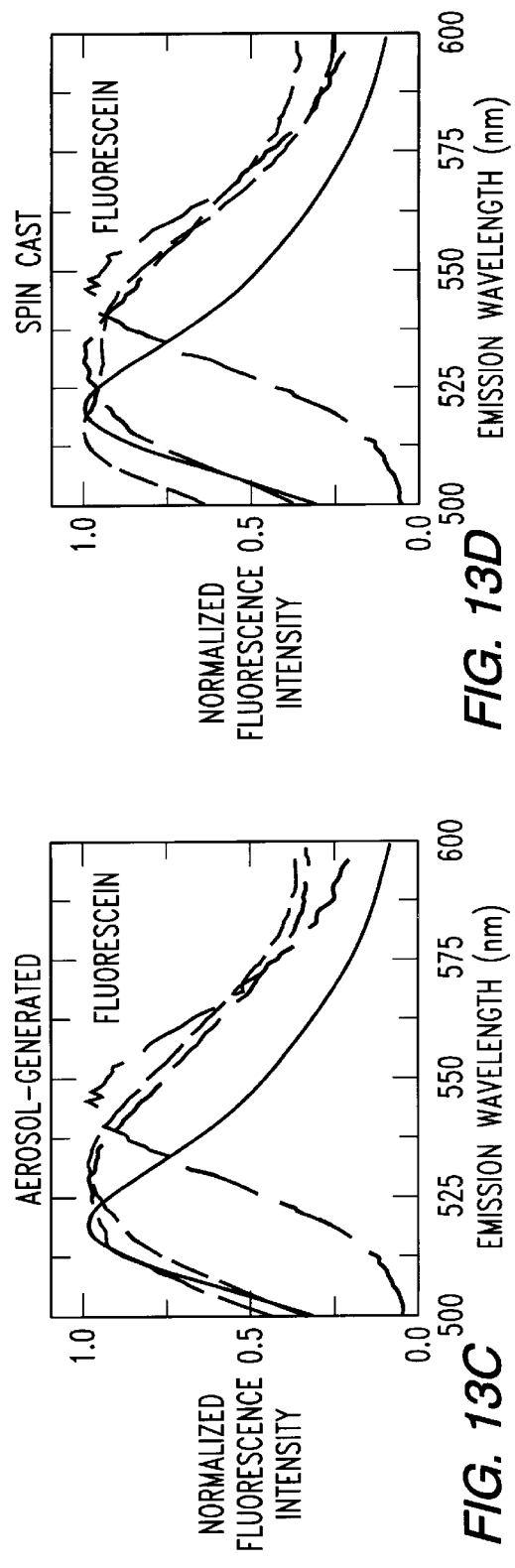
FIGS. 13A–F are steady-state fluorescense emission spectra of various dopants in various materials.

Turning first to the R6G-doped films shown in FIGS. 13A for aerosol generated films and 13B for spin cast films, there are several interesting features. First, the R6G emission maxima is generally insensitive to the physicochemical properties of its local environment. However, it is also known that the R6G emission is sensitive to the extent of R6G aggregation. Sol-gel-derived films when doped with more than 50 $\mu$M R6G is known to have a 16 nm spectral shift. This sol-gel film entrapment decreased R6G monomer aggregation relative to the level seen in aqueous solution. Thus, the slight blue shift observed for the R6G-doped sol-gel films is consistent with sol-gel-induced perturbations to the degree of R6G aggregation.

Sol-gel entrapment of fluorescein (FIGS. 13C for aerosol-generated films and 13D for spin cast films) results in a broadening of the emission spectrum, and the appearance of an emission shoulder to the red of the primary emission seen in ethanol. This result is consistent with the presence of at least two distinct forms of fluorescein within the films. Broadening of the fluorescence spectra is consistent with the interconversion between the fluorescein dianion and anion. The dianion is the most prevalent fluorescein species in ethanol, and its protonation within the sol-gel thin film to form the anion is consistent with the reduced local pH (~5) within the sol-gel composite surrounding the fluorescein molecules. Additional differences between the fluorescein emission spectra associated with the spin-cast and aerosol-generated films indicate that the deposition method can be used to modulate the local microenvironment surrounding the entrapped fluorescein molecules.

Figure 13E:
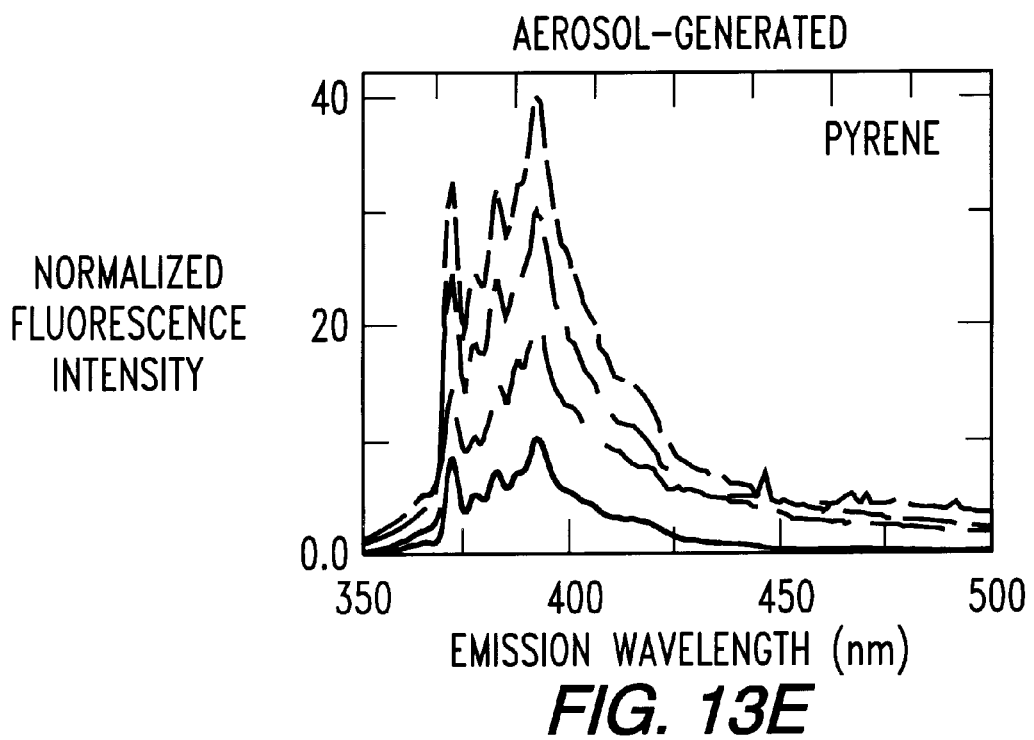
Figure 13F:
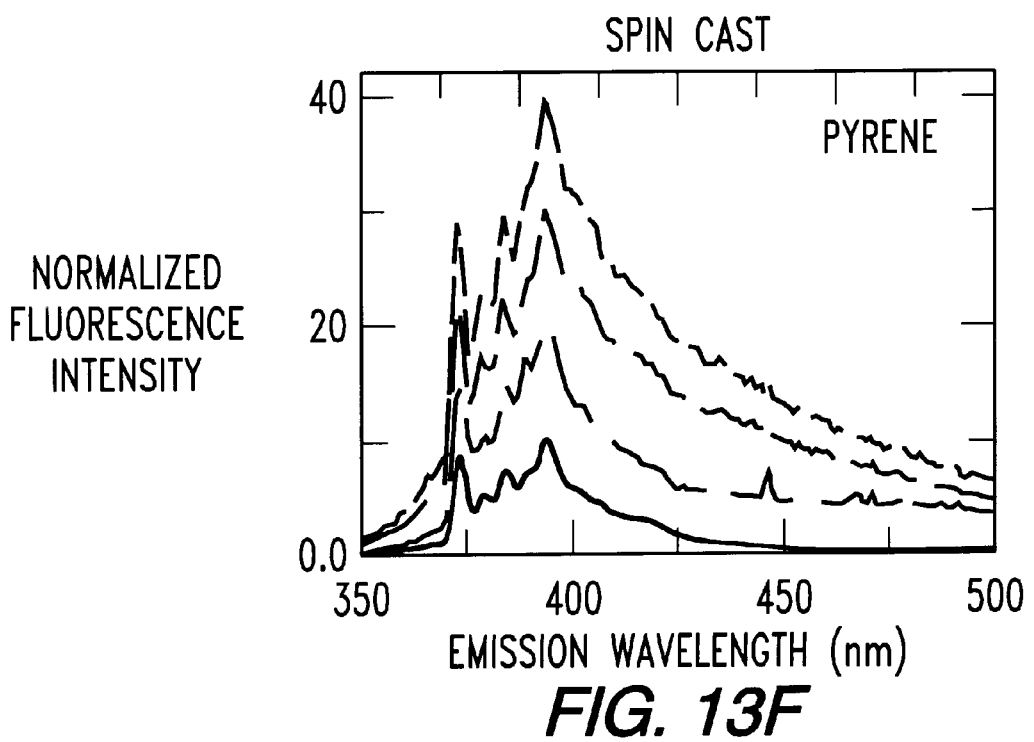

Emission spectra from the pyrene-doped films are shown in the FIGS. 13E for aerosol-generated films and 13F for spin cast films. The pyrene emission spectra possess several well-defined vibronic features in the 370–410 nm range and the intensity ratio of the $I_1$ to $I_3$ peaks ($I_1/I_3$) provides a measure of the physicochemical properties surrounding the local pyrene environment. As examples, the pyrene $I_1/I_3$ values range from 0.41 in the gas phase to 1.95 in dimethylsuffoxide. Thus, $I_1/I_3$ yields a convenient "scale" of the average dipolarity surrounding the pyrene molecule. The $I_1/I_3$ values for pyrene entrapped within or adsorbed to the various sol-gel-derived film types are summarized in Table 3. These data illustrate how the choice of deposition method influences the local physicochemical properties surrounding the pyrene dopant.

TABLE 3

| TEOS:water molar ratio | TEOS (aerosol) | TEOS (spin coated) |
|---|---|---|
| Sol-gel Entrapped Pyrene ($I_1/I_3$) ratios | | |
| Pyrene in ethanol | 1.10 ± 0.01 | |
| 1:2 | 1.16 ± 0.04 | 0.789 ± 0.03 |
| 1:4 | 1.19 ± 0.04 | 0.960 ± 0.04 |
| Sol-gel Adsorbed Pyrene ($I_1/I_3$) ratios | | |
| 1:2 | 0.973 ± 0.04 | 0.869 ± 0.03 |
| 1:4 | 1.01 ± 0.05 | 0.875 ± 0.04 |
| Pyrene adsorbed to clean silica | 0.852 ± 0.04 | 0.852 ± 0.04 |
| Tr-EOS-$C_8$ water molar ratio | Tr-EOS-$C_8$ (aerosol) | TrEOS-$C_8$ (spin coated) |
| 1:3 | 0.640 ± 0.01 | 0.607 ± 0.03 |

The association of pyrene monomers to form excited-state dimers (excimers) is well known. An excimer is indicated by a broad structureless emission in the 425–500 nm spectral range. The pyrene emission spectra (see FIGS. 13E and 13F) for the spin cast films exhibits more of an "excimer-like" emission feature relative to the aerosol-generated films. This phenomena is consistent with our R6G results (see FIGS. 13A and 13B), suggesting sol-gel-induced perturbations to the intermolecular aggregation process to an extent that depends on the film preparation method. Specifically, spin coating yields more pyrene association when compared with aerosol-generated architectures.

A more complete analysis of the pyrene $I_1/I_3$ ratios (Table 3) reveal several interesting trends. First, the $I_1/I_3$ values for pyrene molecules entrapped within the aerosol-generated TEOS films are in all cases greater compared to pyrene molecules sequestered in a spin cast film but are reasonably close to the $I_1/I_3$ value in neat ethanol. This suggest that the local environment surrounding pyrene in the aerosol-derived TEOS films is more dipolar compared to the spin cast TEOS films. Second, the $I_1/I_3$ for pyrene entrapped within the 1:2 TEOS-derived spin-cast films is less than the value seen for pyrene adsorbed to the bare silica substrate. This is consistent with a much less dipolar environment within the 1:2 TEOS spin cast film than is encountered at even a clean silica surface. Third, the $I_1/I_3$ for pyrene within the 1:4 TEOS spin-cast films is statistically greater than the value for the aerosol-generated TEOS film. Again, the dipolarity within the aerosol-deposited film is greater than the spin cast film. Fourth, there is no significant difference sensed by pyrene molecules (based on $I_1/I_3$) within 1:2 and 1:4 TEOS films produced by the aerosol generation scheme. This demonstrates that the microdomain surrounding the pyrene in these films remains at a relatively high dipolarity regardless of the water level. Interestingly, the aerosol film dipolarity ($I_1/I_3$=1.16–1.19) is slightly greater than that of neat ethanol ($I_1/I_3$=1.10).

Statistical differences in the relative % C levels were also observed between aerosol-generated and spin-cast films prepared from identical sol-gel stock solutions. Differences in the film surface carbon coverage should alter the film surface polarity, and thus influence the physicochemical properties and intermolecular interactions to occur at the film surface. To investigate this issue in more detail, neat sol-gel films were prepared using the aforementioned protocols and incubated in 0.5 $\mu$M pyrene solutions (in ethanol) for 1 h, rinsed and allowed to dry. The emission specra from the adsorbed pyrene molecules were then acquired, and the $I_1/I_3$ ratios recorded (Table 3). For comparison, the $I_1/I_3$ value for pyrene adsorbed to a bare fused-silica substrate is also reported.

Inspection of the adsorbed pyrene results show that the TrEOS-$C_8$-derived film surfaces are significantly less dipolar when compared to either a TEOS-derived sol-gel film (1:2 or 1:4) or bare silica. This result indicates that the pyrene molecules adsorbing to the sol-gel films are encountering a significantly less dipolar microdomain at the surface of the TrEOS-$C_8$-derived films. This conclusion is fully consistent with the data Tables 2.2 and 2.3, demonstrating that the spin-cast TrEOS-$C_8$-derived films exhibited a 12% greater relative carbon level at the surface relative to the aerosol-generated films. The adsorbed pyrene data also reveal that the dipolarity of all film surfaces is generally lower than the corresponding bulk film measurements. Again, this is consistent with the Tables 2.2 and 2.3 and FIGS. 11 and 12 results wherein carbon was found to be segregated at the surface of all film types.

One additional aspect of using pyrene to probe the sol-gel-derived thin films properties is associated with its relatively long excited-state fluorescence lifetime and the fact that it can be effectively quenched by $O_2$. As a result, one can exploit the pyrene (Py) fluorescence to obtain information on the efficiency of $O_2$ quenching ($Py°+O_2 \rightarrow Py+O_2$) and the accessibility of the sol-gel-sequestered pyrene molecules to quencher/analyte.

Figure 14A:
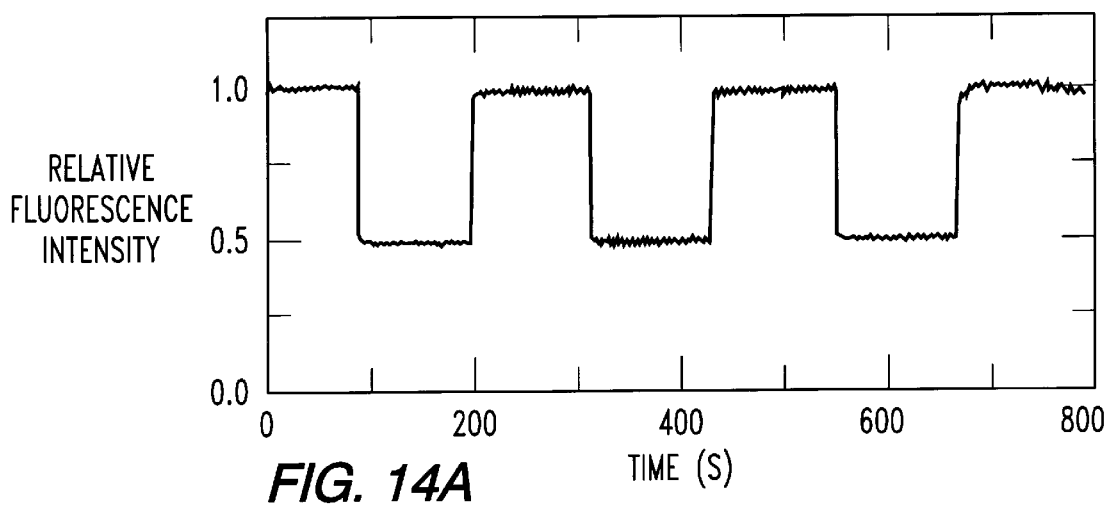
FIGS. 14A–C are the fluorescense response of pyrene-doped sol-gel derived films subjected to $N_2$ and $O_2$ atmospheres.
Figure 14B:
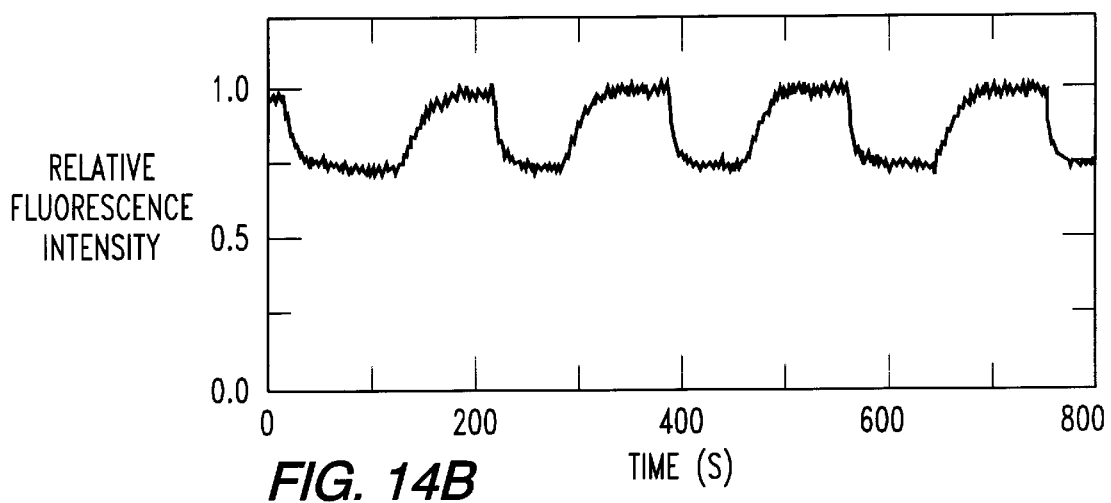
Figure 14C:
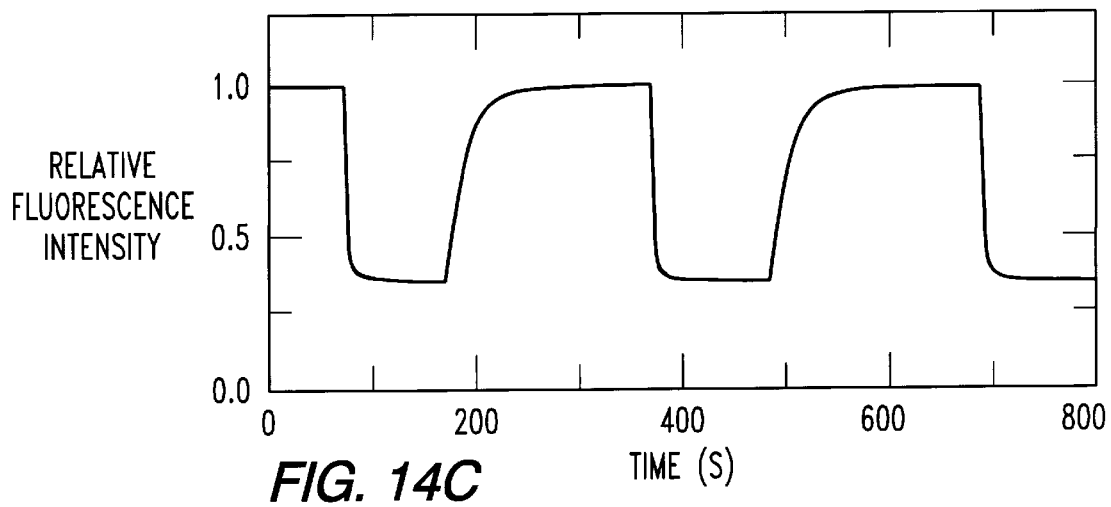

To assess the potential of the aerosol-deposited sol-gel-derived thin films as sensing platforms, we carried out a limited set of experiments on aerosol-generated, spin-cast, and dip-cast films subjected to gaseous $N_2$ and $O_2$ atmospheres. The results of these experiments are presented in FIGS. 14A–C. Several aspects of these data merit special mention. First, pyrene molecules entrapped within the aerosol-deposited sol-gel-derived thin film (FIG. 14A) are quenched by $O_2$. Second, the response times ($O_2 \rightarrow N_2$ and $N_2 \rightarrow O_2$) for the aerosol-based film are significantly less than 1 s. The aerosol film response time is clearly several-fold superior to the response times associated with spin cast (FIG. 14B) and dip cast sol-gel-derived thin films (FIG. 14C). Finally, the response for all three films is completely reversible; however, the $O_2 \rightarrow N_2$ response is at least one order-of-magnitude faster for the aerosol-generated films compared to the other film types (compare FIG. 14A to FIGS. 14B and 14C).

It will thus be seen that the objects set forth above, among those made apparent from the preceding description, are efficiently obtained. Since certain changes may be made in carrying out the above invention and in the constructions set forth without departing from the scope of the invention, it is intended that all matter contained in the above description or shown in the accompanying drawings be interpreted as illustrative and not in a limiting sense. It is also to be understood that the following claims are intended to cover all of the generic and specific features of the invention herein described, and all statements of the scope of the invention, which, might be said to fall therebetween.

What is claimed is:

1. A sensor comprising:
    a substrate overlayed with a first sol-gel layer;
    a chemical sensing species that binds to a particular analyte and is deposited as a layer upon said first sol-gel layer; and
    a thin film of a second sol-gel layer overlaying and immobilizing said chemical sensing species such that said chemical sensing species exhibits a significant portion of its intrinsic function;
    wherein the chemical sensing species, the first sol-gel layer and the second sol-gel layer are all independent and distinct layers from each other.

2. The sensor according to claim 1 wherein said chemical sensing species is polyclonal antifluorescein.

3. The sensor according to claim 1 wherein said thin film of said second sol-gel layer maintains its molecular structure.

4. The sensor according to claim 1 wherein said substrate is polymorphic.

5. The sensor according to claim 1 further comprising a second sensor overlaying said first sensor.

6. The sensor according to claim 1 wherein said first and second sol-gel layers are crack-free.

7. The sensor according to claim 1 wherein said second sol-gel layer has a thickness of less than 1 micron.

8. The sensor according to claim 1 wherein said substrate is monomorphic.

9. A sensor comprising:
    a first substrate overlayed with a first sol-gel layer;
    a first chemical sensing species that binds to a particular analyte and is deposited as a layer upon said first sol-gel layer; and
    a thin film of a second sol-gel layer overlaying and immobilizing said first chemical sensing species such that said first chemical sensing species exhibits a significant portion of its intrinsic function;
    a second substrate overlaying the second sol-gel layer and overlayed with a third sol-gel layer;
    a second chemical sensing species different than said first chemical sensing species that binds to a particular analyte and is deposited as a layer upon said third sol-gel layer; and
    a thin film of a fourth sol-gel layer overlaying and immobilizing said second chemical sensing species such that said second chemical sensing species exhibits a significant portion of its intrinsic function;
    wherein the first and second chemical sensing species, the first sol-gel layer and the second sol-gel layer, third sol-gel layer and fourth sol-gel layer are all independent and distinct layers from each other.

10. A sensor comprising:
    a substrate overlayed with a first sol-gel layer;
    a first chemical sensing species that binds to a first particular analyte and is deposited upon said first sol-gel layer;
    a thin film of a second sol-gel layer overlaying and immobilizing said first chemical sensing species such that said first chemical sensing species exhibits a significant portion of its intrinsic function;
    a second chemical sensing species that binds to a second particular analyte and is deposited upon said second sol-gel layer; and
    a thin film of a third sol-gel layer overlaying and immobilizing said second chemical sensing species such that said second chemical sensing species exhibits a significant portion of its intrinsic function;

wherein the first chemical sensing species, the second chemical sensing species, the first sol-gel layer, the second sol-gel layer and the third sol-gel layer are all independent and distinct layers from each other.

11. The sensor of claim 10 wherein said first and second particular analytes are different.

12. The sensor of claim 10 wherein said second and third sol-gel layers maintain their molecular structure.

13. The sensor of claim 10 wherein said substrate is polymorphic.

14. The sensor of claim 10 wherein said first, second and third sol-gel layers are crack-free.

15. The sensor of claim 10 wherein each of the second and third sol-gel layers has a thickness of less than 1 micron.

16. The sensor of claim 10 wherein each of the second and third sol-gel layers is hydrophilic.

17. The sensor of claim 10 wherein said substrate is monomorphic.

18. The sensor of claim 10 wherein each of the second and third sol-gel layers is hydrophobic.

* * * * *